US012544314B2

United States Patent
Bonilla et al.

(10) Patent No.: US 12,544,314 B2
(45) Date of Patent: Feb. 10, 2026

(54) SYSTEM AND METHOD FOR MEDICATION COMPLIANCE

(71) Applicants: Alan Bonilla, Doral, FL (US); Damarys Respeto, Doral, FL (US)

(72) Inventors: Alan Bonilla, Doral, FL (US); Damarys Respeto, Doral, FL (US)

( * ) Notice: Subject to any disclaimer, the term of this patent is extended or adjusted under 35 U.S.C. 154(b) by 288 days.

(21) Appl. No.: 18/319,721

(22) Filed: May 18, 2023

(65) Prior Publication Data

US 2023/0372205 A1 Nov. 23, 2023

Related U.S. Application Data

(60) Provisional application No. 63/343,243, filed on May 18, 2022.

(51) Int. Cl.

| | |
|---|---|
| ***G16H 20/13*** | (2018.01) |
| ***A61J 1/03*** | (2023.01) |
| ***A61J 7/00*** | (2006.01) |
| ***A61J 7/04*** | (2006.01) |

(52) U.S. Cl.

CPC ............... *A61J 7/0481* (2013.01); *A61J 1/03* (2013.01); *A61J 7/0007* (2013.01); *A61J 7/0069* (2013.01); *G16H 20/13* (2018.01); *A61J 2200/30* (2013.01); *A61J 2205/20* (2013.01); *A61J 2205/40* (2013.01); *A61J 2205/50* (2013.01)

(58) Field of Classification Search

CPC . G16H 20/13; A61J 7/02; A61J 7/0084; A61J 7/0454

USPC .............................................................. 705/2

See application file for complete search history.

(56) References Cited

U.S. PATENT DOCUMENTS

2003/0086338 A1* 5/2003 Sastry .................... G16H 20/13 368/10
2006/0058917 A1* 3/2006 Vonk ..................... A61J 7/0481 700/236
2007/0007162 A1* 1/2007 Buller .................. A61J 7/0069 206/534

OTHER PUBLICATIONS

Reddit request from bobusdoleus, "[Request] Pill carrier thing with compartments for multiple daily doses that doesn't have flimsy plastic hinges", dated "6 yr. ago" (therefore, 2019), downloaded Oct. 10, 2025 (Year: 2019).*

* cited by examiner

*Primary Examiner* — Scott D Gartland
(74) *Attorney, Agent, or Firm* — Peter A. Sullivan; Stephen J. Kenny; Foley Hoag LLP

(57) ABSTRACT

A system for a device for maintaining medication compliance. The device includes a tray base having a plurality of recesses aligned in a plurality of rows and columns and a tray drawer disposed within a hollow portion of and slideably coupled to the tray base. The device includes a plurality of pill compartments coupled to the tray base in a plurality of corresponding recesses. The pill compartments have a lid disposed on the top portion of pill compartment, rotatably coupled to the back wall and releaseably coupled to the front wall. The pill compartments can be coupled together. The device includes a plurality of time indicator compartments that are coupled to the tray base 104 and the pill compartments. Each of the time indicator compartments includes a time set component.

11 Claims, 17 Drawing Sheets

FORM FOR PARTICIPANTS

1104

Will need to register

- Name:
- Email:
- Who is authorize to receive copies of the Medication Schedules:
- Name of Medication (s):
- Medication Dosage, frequency:
- Instructions (Ex twice a day and time):
- Color, shape, If its Eye drop what color is the Tab:
- - Input Time and Date
- Different rates + Shipping and Handling ( Via email in PDF file) :
  - One Time Only
  - Monthly Membership
  - Annual Membership rate -

FIG. 11

SYSTEM AND METHOD FOR MEDICATION COMPLIANCE

CROSS-REFERENCE TO RELATED APPLICATIONS

This application claims the benefit of priority to U.S. Provisional Application No. 63/343,243, titled "SYSTEM AND METHOD FOR MEDICATION COMPLIANCE," filed on May 18, 2023, the entire contents of which are incorporated by reference herein.

BACKGROUND OF THE DISCLOSED SUBJECT MATTER

Field of the Disclosed Subject Matter

The disclosed subject matter relates to a system and method for assisting patients in maintaining compliance in taking medication. Particularly, the present disclosed subject matter is directed systems and methods for organization, tracking, and delivery of pill-form medication.

DESCRIPTION OF RELATED ART

Many people have daily medication requirements that require them to take numerous medications per day at different times a day. As the number of medication dosages increases, the likelihood of making a mistake also increases, creating an obstacle to compliance.

A second obstacle for those who take multiple medications is the inability to explain, in lay terms, which medication is for which treatment. Patients more commonly will refer to a medication to treat a condition as a "heart pill" or a "blood pressure pill" than to refer to their brand or generic names.

A third obstacle is technology, or the difficulty of portions of the medication-taking populations from navigating technology solutions aimed at some of these problems. Many people do not have the technology skills to navigate the current mobile or desktop applications and websites available for some of these issues. Power and internet connectivity is a related problem, especially in areas that are susceptible to unreliable power and internet infrastructure and in areas of the world that are less developed or urban.

There thus remains a need for an efficient and economic method and system for maintaining compliance with taking medication and tracking which medication is being taken at what intervals over a period of time. There also therefore remains a need for an efficient and economic method and system to use for someone with the inability or limited ability to utilize a web/mobile application in maintaining compliance for medication.

SUMMARY OF THE DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a system for maintaining medication compliance including a tray base, wherein the tray base comprises a plurality of recesses aligned in a plurality of rows and columns, each recess comprising a first anchor mechanism, at least one pill compartment, each pill compartment having a second anchor mechanism disposed on a compartment bottom configured to couple to the first anchor mechanism, the pill compartment having a lid disposed on a top portion of the pill compartment, a compartment coupling mechanism disposed on the pill compartment configured, the compartment coupling mechanism configured to couple to a corresponding compartment coupling mechanism of an adjacent pill compartment and at least one time indicator compartment, the time indicator compartment having a time set component configured to display a time of day disposed on a top portion each time indicator compartment, the time indicator compartment having a second anchor mechanism disposed on a bottom portion of the time indicator compartment and the pill compartment coupling mechanism disposed on a wall of the time indicator compartment.

To achieve these and other advantages and in accordance with the purpose of the disclosed subject matter, as embodied and broadly described, the disclosed subject matter includes a method for medication compliance including inputting user information into a form, wherein the user information comprises at least a medication schedule, aggregating user medical information, wherein the medical information has at least a medication and a dosage, generating an insert having medication instructions based on the medication schedule, medication and the dosage and generating the insert within a medication compliance device having a tray base, at least one pill compartment, disposed on the tray base, the pill compartment having a lid disposed on a top portion of the pill compartment, a compartment coupling mechanism disposed on the pill compartment, the compartment coupling mechanism configured to couple to a corresponding compartment coupling mechanism of an adjacent pill compartment and at least one time indicator compartment, the time indicator compartment having a time set component configured to display a time of day.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

FIG. 11 is a portion of a user interface to input medication information for the insert of one embodiment of the invention.

DETAILED DESCRIPTION OF AN EXEMPLARY EMBODIMENT

Reference will now be made in detail to exemplary embodiments of the disclosed subject matter, an example of which is illustrated in the accompanying drawings. The method and corresponding steps of the disclosed subject matter will be described in conjunction with the detailed description of the system.

Figure 1:
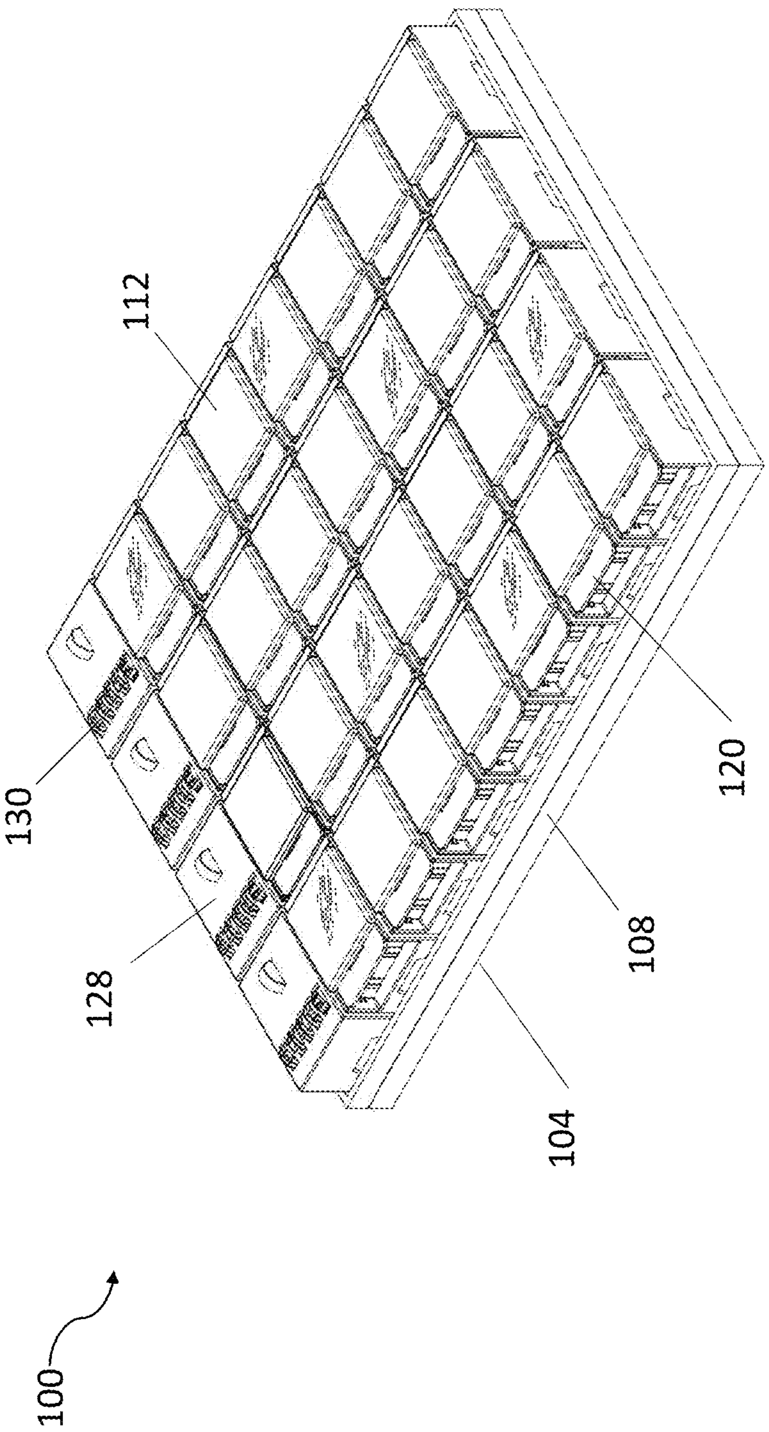
FIG. 1 is a perspective view of the top of a pill organizer tray of one embodiment of the invention.

The methods and systems presented herein may be used for medication compliance maintenance. The disclosed subject matter is particularly suited for organizing, tracking, displaying, and containing a plurality of medications directed by a doctor for a patient to administer to themselves. For purpose of explanation and illustration, and not limitation, an exemplary embodiment of the system in accordance with the disclosed subject matter is shown in FIG. 1 and is designated generally by reference character 100. Similar reference numerals (differentiated by the leading numeral) may be provided among the various views and FIGS. presented herein to denote functionally corresponding, but not necessarily identical structures.

A system for assisting with administration of medication and medication compliance is described. A pill organizing tray may contain twenty-eight compartments, with seven columns for each day of the week and four rows representing times of the day in which pills are to be taken. The medication tray compartments are disengageable from the tray base to allow for removal, for example, to bring selected compartment to medical provider visits. A column adjacent to the pill compartments may include a time set to manual set the time of day in which to take the medication and a pill counter to note the total number of pills to take at that given time. A pill cutter may also be attached to a compartment in one embodiment.

The may be associated with an information insert. The insert is created by providing all medications that are taken in a given week, including a physical description of the color and pill shape as described herein. This information is used by the system to associate the medication type with an icon showing the pill color, shape and number per dosage, a lay description of the medication and an icon representing the anatomical system the medication is designed to treat. The system of the invention is designed to improve and facilitate adherence to the prescribed therapy given by doctors. This will benefit both patients and caregivers via a customized process and tool.

Referring now to FIG. 1, system 100 for medication compliance is shown in perspective view. System 100 includes a tray base 104. The tray base 104 is disposed at the bottommost portion of system 100 and can have raised walls around its perimeter for further security of compartments on top and within the tray. The tray base 104 includes a plurality of recesses that can be rectangular or semi rectangular in planform shape. The plurality of recesses may be disposed in regular rows and columns to create a grid of recesses within the tray base 104. Each recess can include a first anchor component 106. The first anchor component 106 may be a hole, a recess, slot, or other cavity in which a corresponding component may be inserted and create friction between the two components and therefore temporarily coupling the components together.

System 100 includes a tray drawer 108 disposed within a partially or totally enclosed interior volume. The tray drawer 108 is slideably coupled within the tray base 104 such that it can be pulled out by a user to reveal a large portion of the interior of the drawer and storage of a plurality of objects. For example and without limitation, one or more sheets of paper may be stored in the tray drawer 108 such as the insert 1116 discussed later in this disclosure. The tray drawer 108 may include a locking mechanism to prevent unauthorized access or to prevent the tray drawer 108 from opening due to forces imparted on it such as gravity, being knocked over, dropped, etc.

System 100 may include a plurality of pill compartments 112. Each of the plurality pill compartments 112 includes a front wall and a back wall disposed opposite and parallel to each other. Each of the front and back wall are connected therebetween by two sidewalls coupled at each end and disposed opposite and parallel from each other to create a four walled rectangle. Each pill compartment includes a compartment floor disposed thereunder perpendicular to and terminating at each of the walls to form an open-topped container. This is only an embodiment of the pill compartments 112, and does not seek to limit the shape of the pill compartments 112 to rectangular. Each of the plurality of pill compartments 112 may be the corresponding planform shape as each of the recesses within the tray base 104. Each of the pill compartments 112 may include geometry configured to couple itself to the tray base 104, such as the corresponding peg to match the hole in the recess, the boss to fit in the slot, or a matching hook, in embodiments. Each compartment has a bottom side that contains interlocking pegs to connect to a bottom tray. In one embodiment, the interlocking pegs are the same across the columns and rows of the bottom side of the compartments. In another embodiment, the pegs are configured to differ across rows, columns or both rows and columns like fitting pieces in a puzzle. In some embodiments the pegs have a fixed length and/or orientation/angle. In some embodiments the pegs can be adjustable in length, and/or orientation/angle, to affirmatively lock the pill compartment to the tray base, with the pin being retracted (e.g. in a telescoping fashion) to permit release and removal of the pill compartments.

Each pill compartment includes a lid 116 disposed on the top portion of pill compartment, rotatably coupled to the back wall and releaseably coupled to the front wall. That is to say that when free to rotate, the lid 116 may be opened to gain access to the interior of the pill compartment. Each pill compartment includes a lid release 120 disposed on the front wall configured to hold the lid 116 closed until released. The lid release 120 may be under spring tension until released by the pressing of a button by a user. For example and without limitation, the user may press a button and the lid 116 may flip open, the user may flick a switch and the lid 116 flips open, or the user may have to manually remove the lid release 120, like a hook, and lift the lid 116 themselves with their fingers. In some embodiments, the release 120 projects laterally outward from the sidewall of the pill compartment; additionally or alternatively, the release can project vertically (and or angularly, e.g. 45 degree) to increase the surface area to facilitate contact with a user's finger.

Each pill compartment may include a compartment coupling mechanism 124 disposed on at least a wall of the compartment configured to mate with adjacent compartment coupling mechanisms 124. Each pill compartment may include a compartment coupling mechanism 124 on each of its four exterior walls. The compartment coupling mechanism 124 may be male or female surface features, e.g., pegs that match up to mirrored holes on adjacent pill compartments 112, bosses and recesses, slots, or the like. Each pill compartment may be configured to create a press fit between adjacent pill compartments 112 and through friction couple the pill compartments 112 together. The adjacent pill containers may be clicked together, slotted together, mechanically fastened or bonded together with adhesive, in embodiments. For example a first pill container can positioned adjacent to a second pill container, with he first pill container slid vertically downward such that the coupling mechanism 124 of the first pill compartment matingly engages the complimentary coupling mechanism of the adjacent/second pill compartment. Each pill compartment may be temporarily or permanently bonded together or to the tray base 104, in embodiments. A plurality of pill compartments 112 may be coupled together without the utilization of the tray base 104 and act as a miniature or partial version of system 100. System 100 can contain twenty-eight compartments. The pill compartments 112 may be arranged seven to a (horizontal) row to correspond to days of the week, and four (vertical) column-wise to represent times of day to ingest the pills therefound, in embodiments. The pill compartments 112 of the tray can be differentiated by day (Sunday through Saturday) or by time of day (e.g., morning, day, dinner, night) through visual indicators, including through use of color coding, symbols or other imagery.

With continued reference to FIG. 1, system 100 includes a plurality of time indicator compartments 128. Each time indicator compartments 128 include a time set component configured to display a time of day disposed on the top portion each time indicator compartment 128. The time set component may include a roll of adjacent numbers on wheels that a user rolls to display a time. The time set component may include an adjustable clock face or a digital clock. Each time indicator compartment 128 may include the same anchor mechanism configured to couple each to the tray base 104 in the same manner as each of the pill compartments 112. Each of the time indicator compartments 128 include at least the compartment coupling mechanism disposed on at least a wall in the same manner as the pill compartments 112. That is to say that any of the plurality of time indicator compartments 128 may be swapped with any of the plurality of pill compartments 112 within the tray base 104 for customization by the user and according to medical requirements. Thus, the time indicator compartments 128 have the same size and shape (or "footprint") as the pill compartments 112.

Figure 2:
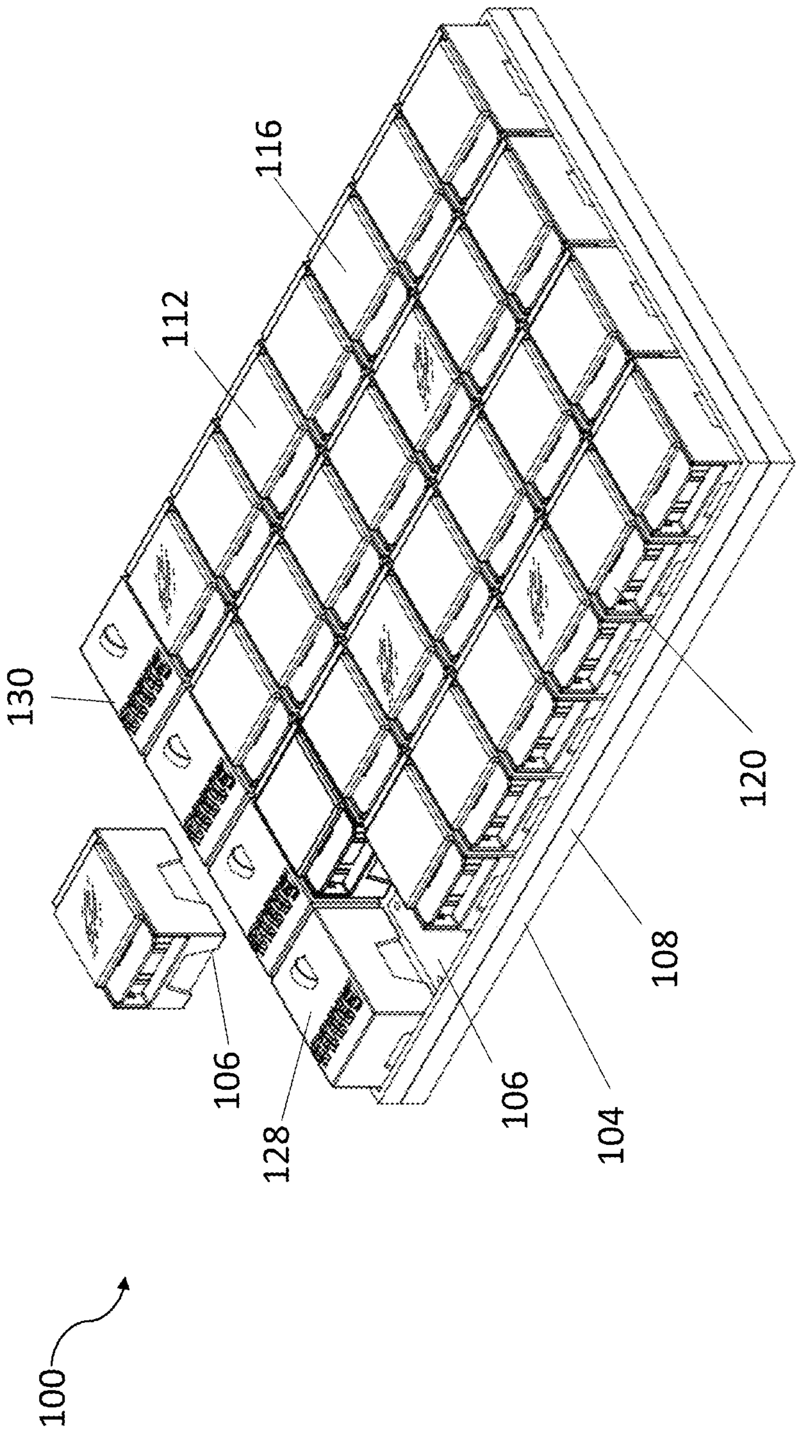
FIG. 2 is a perspective view of the top of a pill organizer tray of one embodiment of the invention with one of the pill compartments 112 removed.

Referring now to FIG. 2, an embodiment of system 100 is shown in isometric view with one of the pill compartments 112 removed from the base tray 104. An embodiment of the tray base 104 allows for removal of individual pill compartments 112. In one embodiment of the tray base 104, the pill compartments 112 have interlocking segments, compartment coupling mechanisms on the side of the compartment to allow interlocking with adjacent compartments such as compartment coupling mechanisms 124 as described herein.

Figure 3:
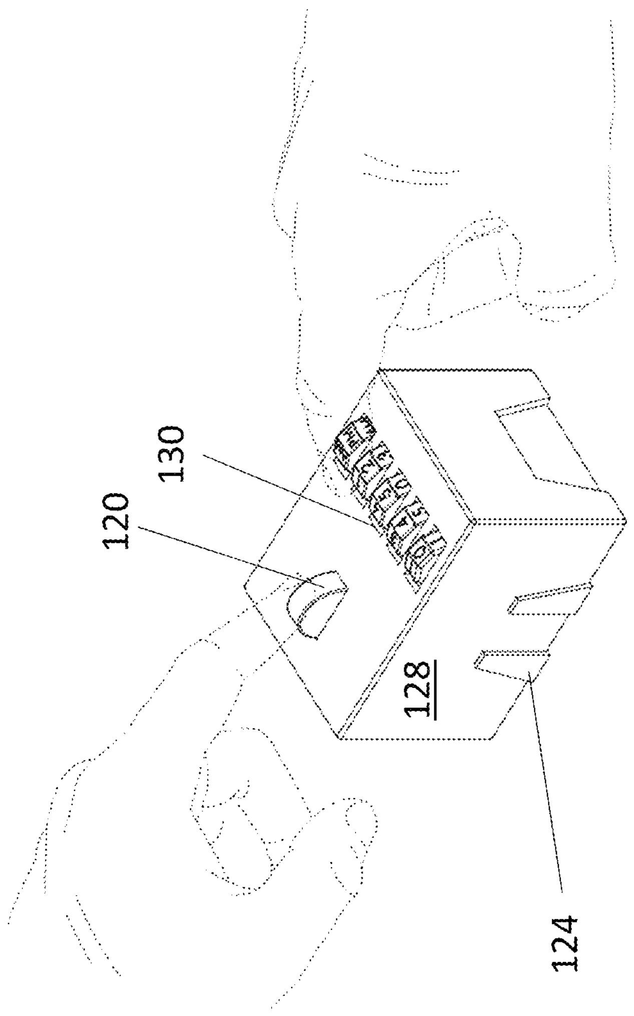
FIG. 3 is a view of the time display unit and the locking mechanism of one embodiment of the invention.
Figure 4:
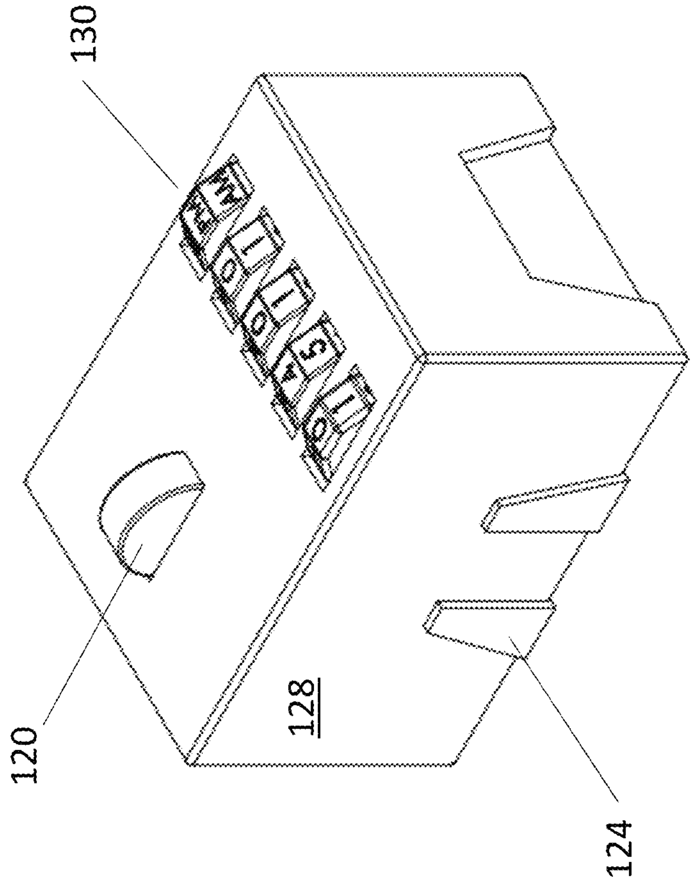
FIG. 4 is a view of the time display dial and the locking mechanism of one embodiment of the invention.
Figure 5:
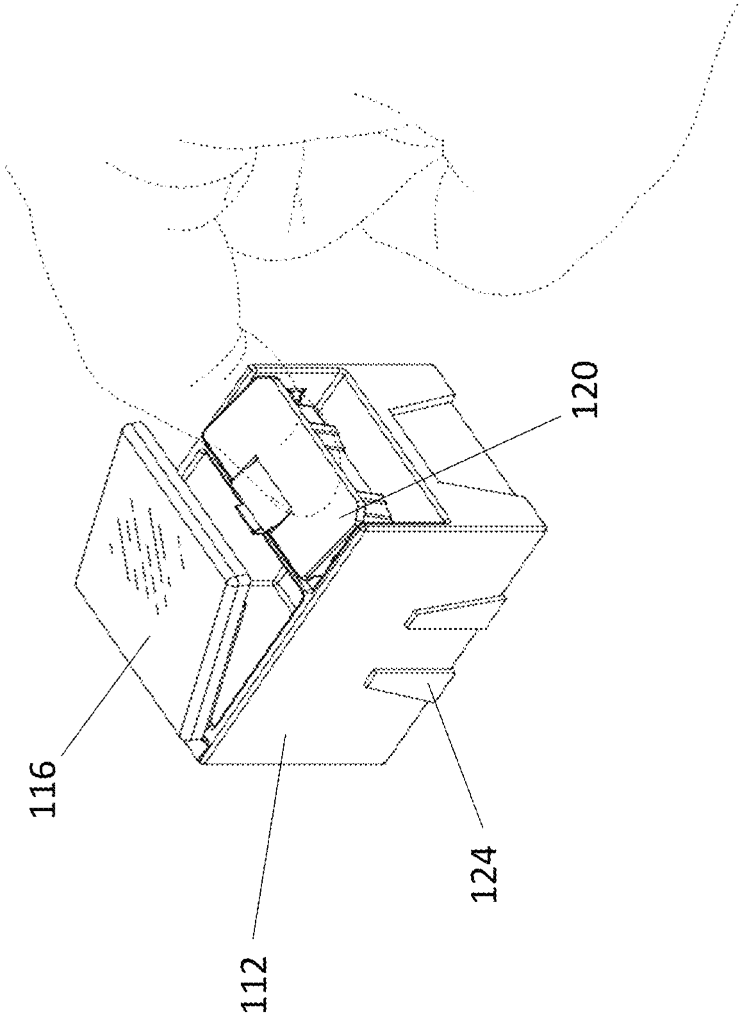
FIG. 5 is a view of a compartment of the pill organizer tray of one embodiment of the invention with the opening mechanism employed to open the compartments.

Referring now to FIG. 3, an embodiment of time indicator compartment 128 is shown in isometric schematic view with phantom lines depicting the user's hands operating the time indicator compartment 128. In various embodiments, the user may initiate the actuation of the time set component 130 to set a time to take the medication, on an embodiment of time indicator compartment 128. In various embodiments, the time set component 130 may be a time dial that has a locking mechanism to prevent the time dial to change and give an incorrect indication of when to take a dose. In various embodiments, the user may depress a button actuator to free the time set component 130, such as the time dials shown on the lid of the time indicator compartment 128 to spin and set the time to take a dosage. FIG. 4 shows the time indicator compartment 128 with the interlocking segments along two of the sides of the time indicator compartment 128.

Figure 16:
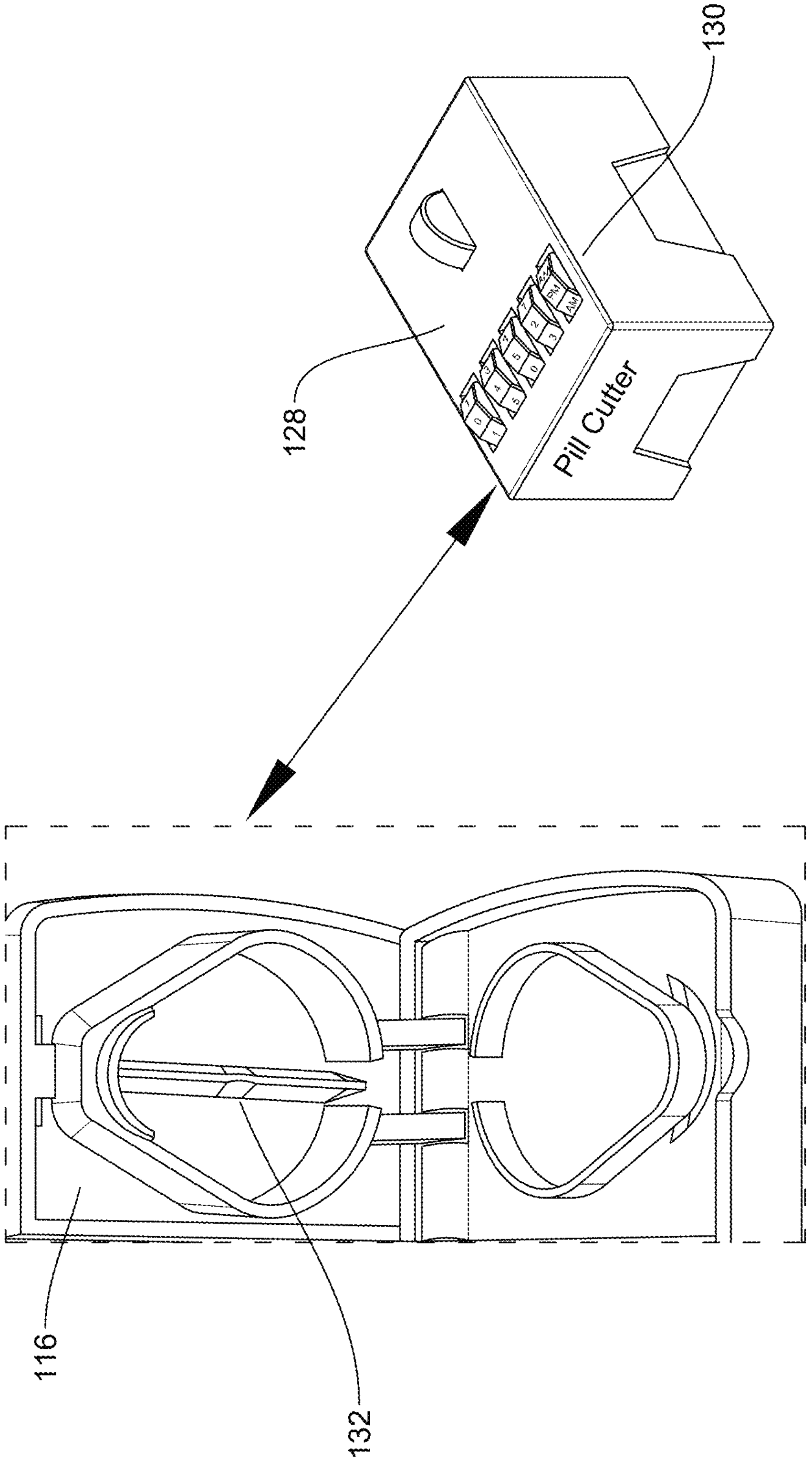
FIG. 16 is a perspective view of a time indicator compartment including a pill cutter disposed within.

In various embodiments, FIG. 16 is a schematic isometric view of the time indicator compartment 128. In various embodiments time indicator compartment 128 may include a lid that rotates or tilts open, as described in reference to the pill compartments. In various embodiments, in an embodiment of the pill organizer tray system 100 includes a time indicator compartment 128 that can only be opened at the correct time of day (e.g. via magnetic lock that is programmed to release at designated times), or when the correct time is inputted. The user may press down on the opening tab to open the top side of the time indicator 128 compartment similarly to the description of the lid 116 in reference to FIG. 1. In various embodiments, the opening tabs can be color coded or otherwise differentiated by day or time of day. In some embodiments, the locking feature of the time indicator compartments 128 can prohibit opening of all, or only select, pill compartments 112. For example, the time indicator compartment 128 for a given row can prevent the pill compartments 112 within that row from being opened until the time set/programed on the time set component 130 is reached—at which time the user can open the time indicator compartment 128 and/or time set component 130. This can advantageously prevent inadvertent over dosing by the patient by consuming improper, or excessive medications from a given pill compartment 112.

The time indicator compartments 128 sides may include compartment coupling mechanism 124 configured to couple adjacent compartments together, for example time indicator compartment 128 and pill compartment 112. In various embodiments, compartment coupling mechanisms may include opposite and interlocking segments, bosses, slots or the like, each configured to be used according to the description of compartment coupling mechanisms herein.

Figure 6:
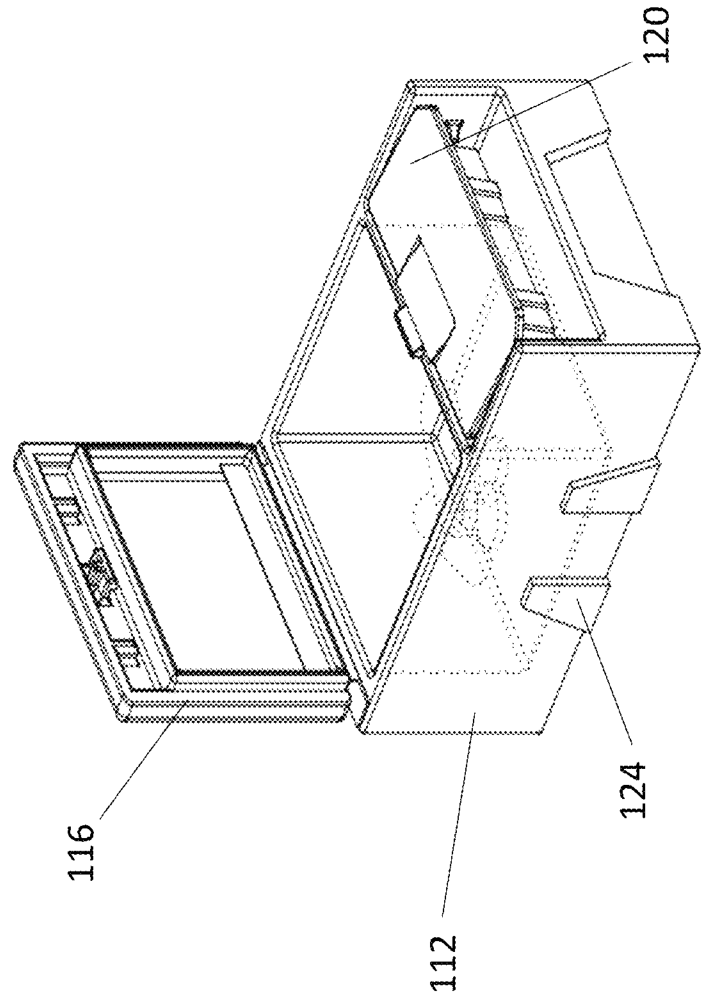
FIG. 6 is a view of a compartment of the pill organizer tray of one embodiment of the invention with the compartment opened.

Referring now to FIG. 6, a schematic isometric representation of the pill compartment 112 in an open position is depicted. Pill compartment 112 may include internal organization within a single compartment. In various embodiments, the internal organization may be a shadow box fit for holding pills or tablets. In various embodiments, the internal organization may include one or more walls configured to split the internal cavity of the compartment. In various embodiments, the internal organization may include recesses or holes so only a certain pill size or shape may pass through the holes or into the recesses, thereby organizing the medication by size and shape. In various embodiments, internal organization may include cups or separate depressions configured to retain the pills or medications by gravity in certain sections of the compartment. In various embodiments, the internal organization may correspond to pill type, time of day, day of week, or any other information associated with the user, so as to separate medication according to the medical instructions provided herein.

Figure 7:
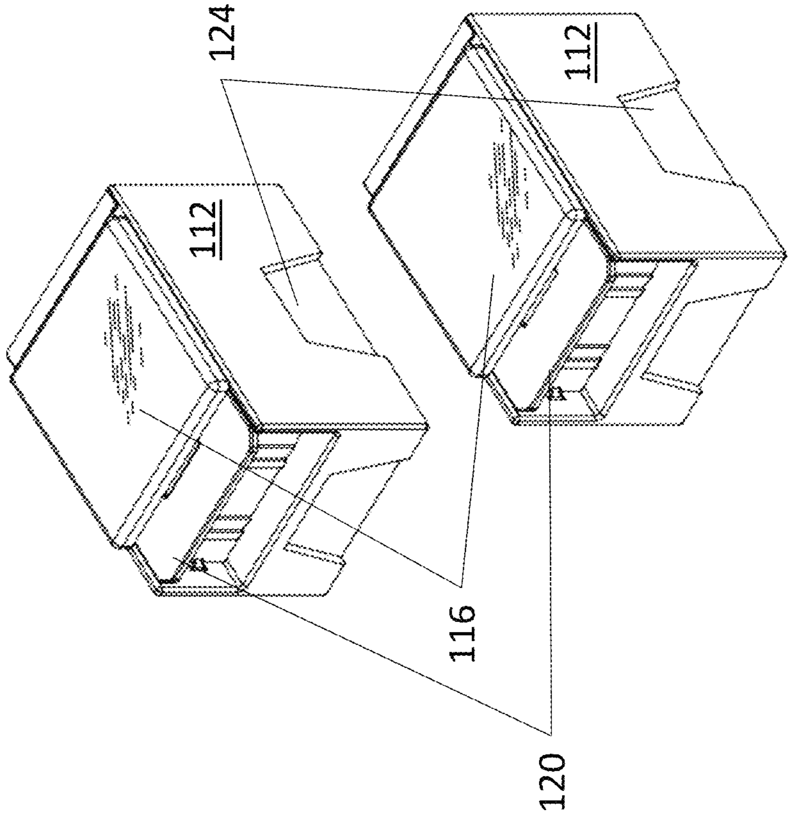
FIG. 7 is a view of two compartments of the pill organizer tray of one embodiment of the invention with the compartment closed with the side of the compartments showing interconnecting segments that allow adjacent compartments to connect to each other.

Referring now to FIG. 7, a schematic isometric representation of two pill compartments 112 for one embodiment of the pill organizer tray with the compartments closed. Note that the pill compartment include a slot on the right hand side of each that correspond to a boss disposed on the left hand side of each of the compartments displayed in FIG. 6, in embodiments. This is only an example and the pill compartments 112 can be coupled together in a plurality of manners, temporarily or permanently.

Figure 8:
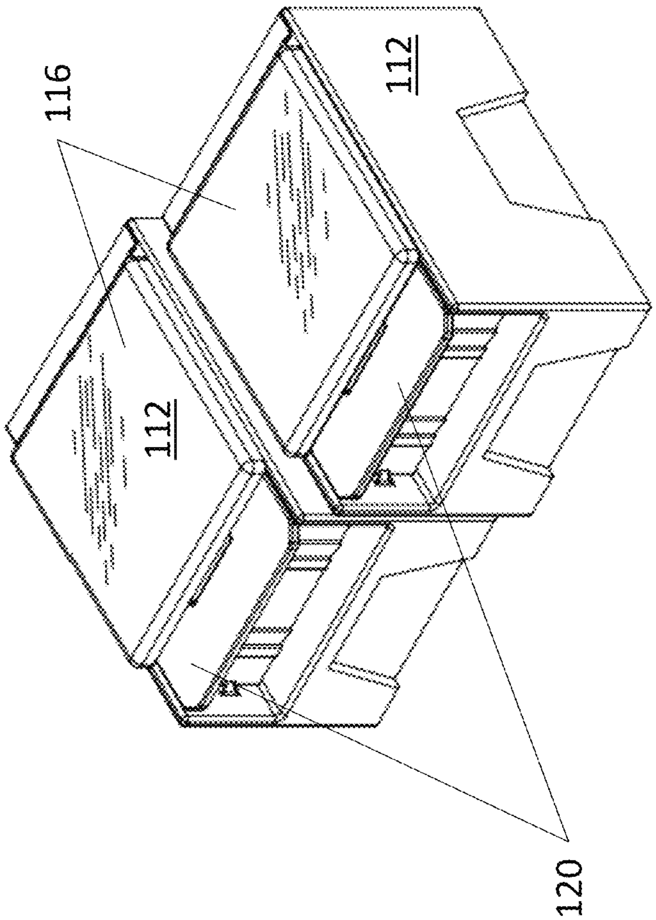
FIG. 8 is a view of two connected compartments of the pill organizer tray of one embodiment of the invention with the compartments closed.

Referring now to FIG. 8, a schematic isometric representation of two pill compartments 112 with the two pill compartments 112 coupled to each other. The pill compartments 112 of the connector are inter-connectable so that the user can take less than the entire system 100 when visiting a medical provider, traveling, or has completed the portion of the week's medication they have left behind.

Figure 9:
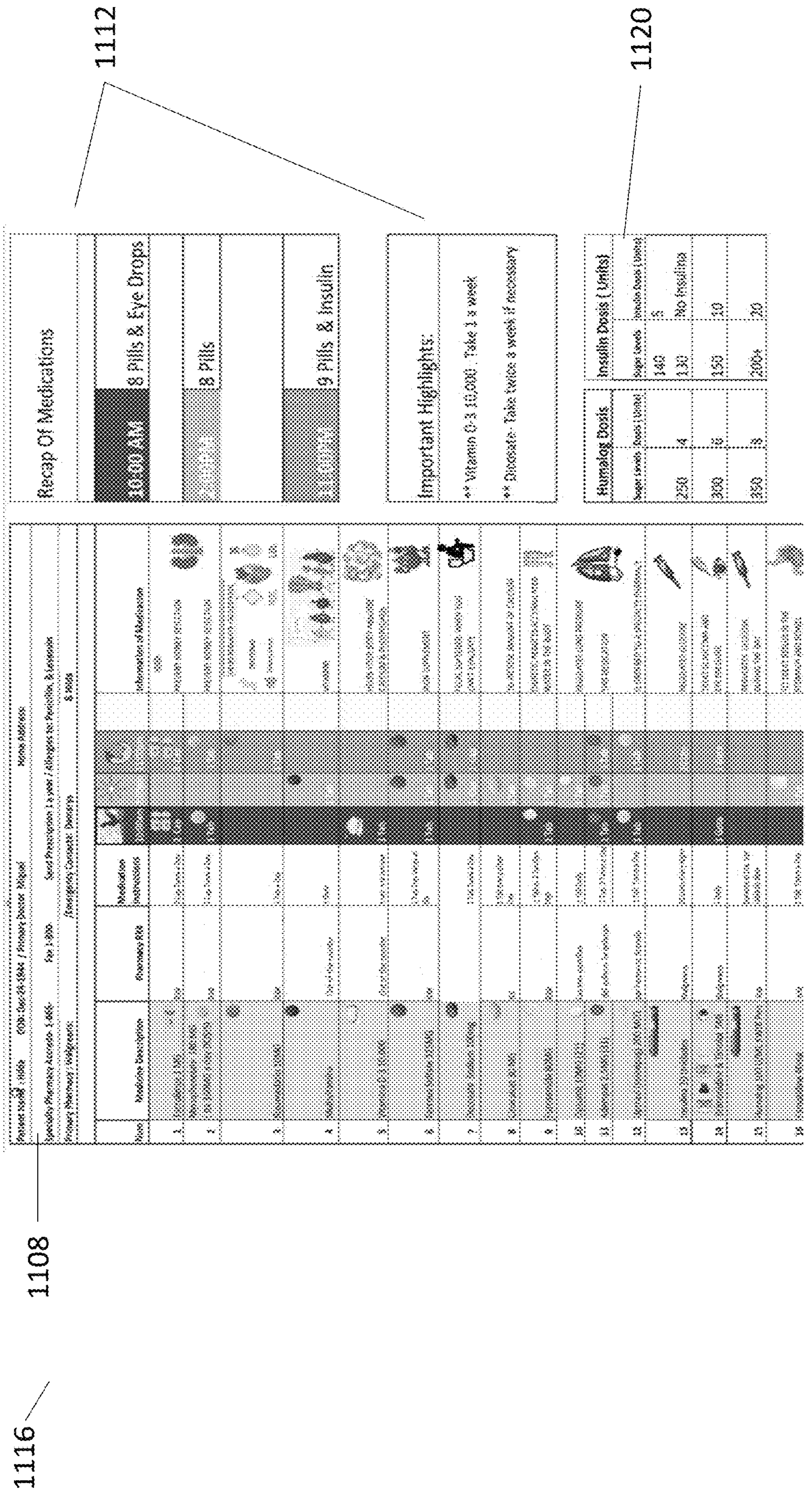
FIG. 9 is a view of a page of an insert for use with the pill organizer tray.
Figure 10:
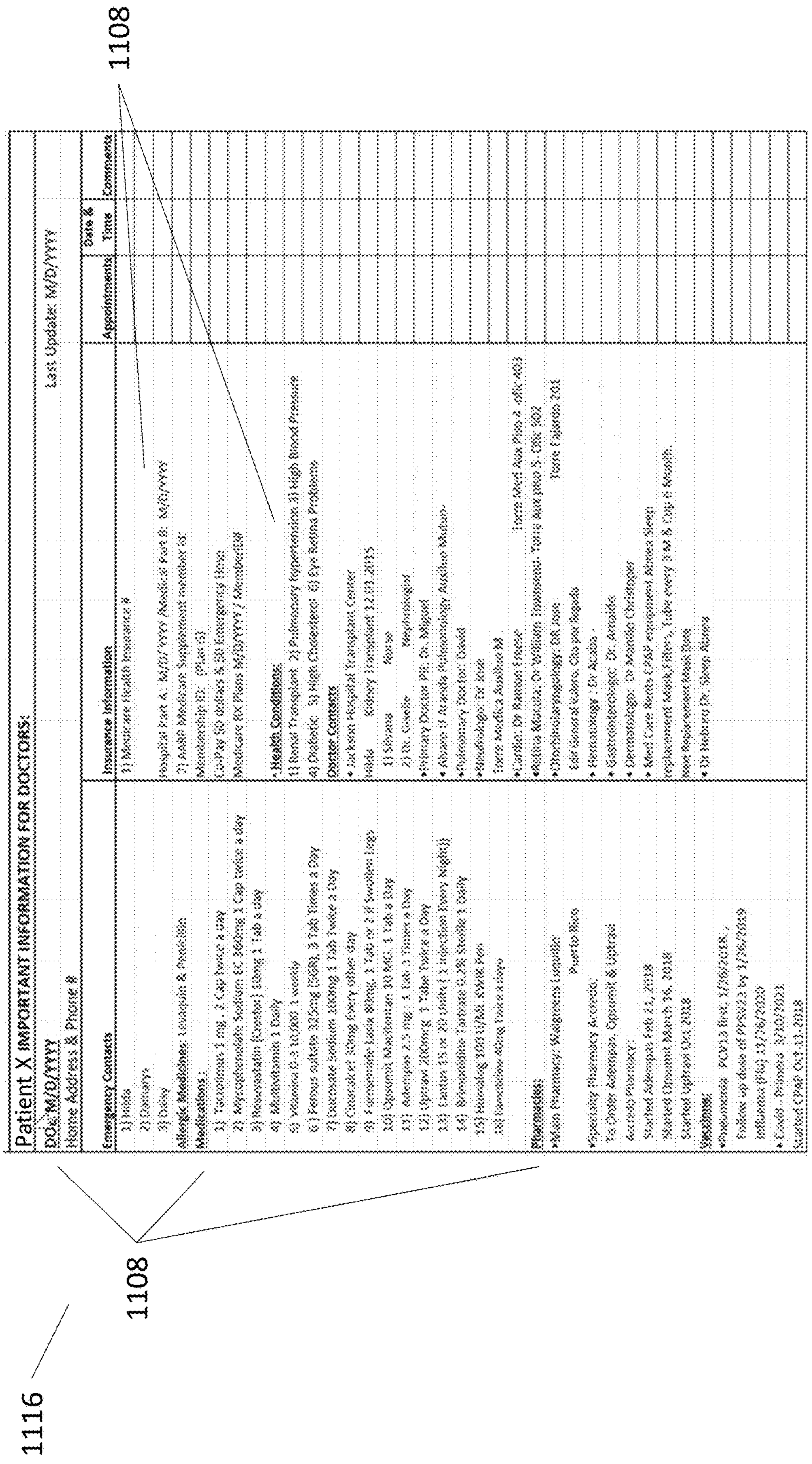
FIG. 10 is a view of a page of an insert for use with the pill organizer tray.

Referring now to FIGS. 9 and 10, depictions of exemplary inserts 1116 generated and used with the system described herein is shown in schematic view. In one embodiment of the invention, the insert 1116 contains a table of the pills that are being taken for the week, with columns for the name of the medication, the prescription number, daily dosage, a representation of how many and when to take the medication, and a lay description of the use of the medication. In some embodiments, there will be symbols used to assist in the description of the use of the medication, e.g., the use of a heart symbol to indicate that the medication is used to treat a heart condition. In another example the insert 1116 may include representations of the medication itself such as photographs, outlines of pills indicating the shape and/or color, a pictorial or symbolic representation to indicate time of day, and the like. In one embodiment, additional information contains summary information about the number of pills taken at a given time of the day or other information pertinent to a particular treatment (e.g., insulin doses for diabetes as show in FIG. 9). In one embodiment of the insert, the columns showing the dosage are color coded to match the color coding of the pill organizing tray such as in the right top hand corner of FIG. 9. The columns include the dosage of each pill being administered in a given dosage time, with the number of pills show by an icon of the pill itself by shape and color, as well as a written description of the dosage, e.g., 2 cap, 1 tab. There may be more than one insert 1116 such as the inserts of FIGS. 9 and 10 being used in tandem.

Referring now to FIG. 10, a page of an insert 1116 is shown in schematic view. This page of the insert 1116 contains health condition, medications taken, medications to avoid because of allergic reactions, medical provide contact information, medical provider appointment dates, pharmacy information, vaccination history, and insurance information. The insert 1116 provides a snapshot of the patient's status to allow medical providers to make decisions on treatments.

Figure 12:
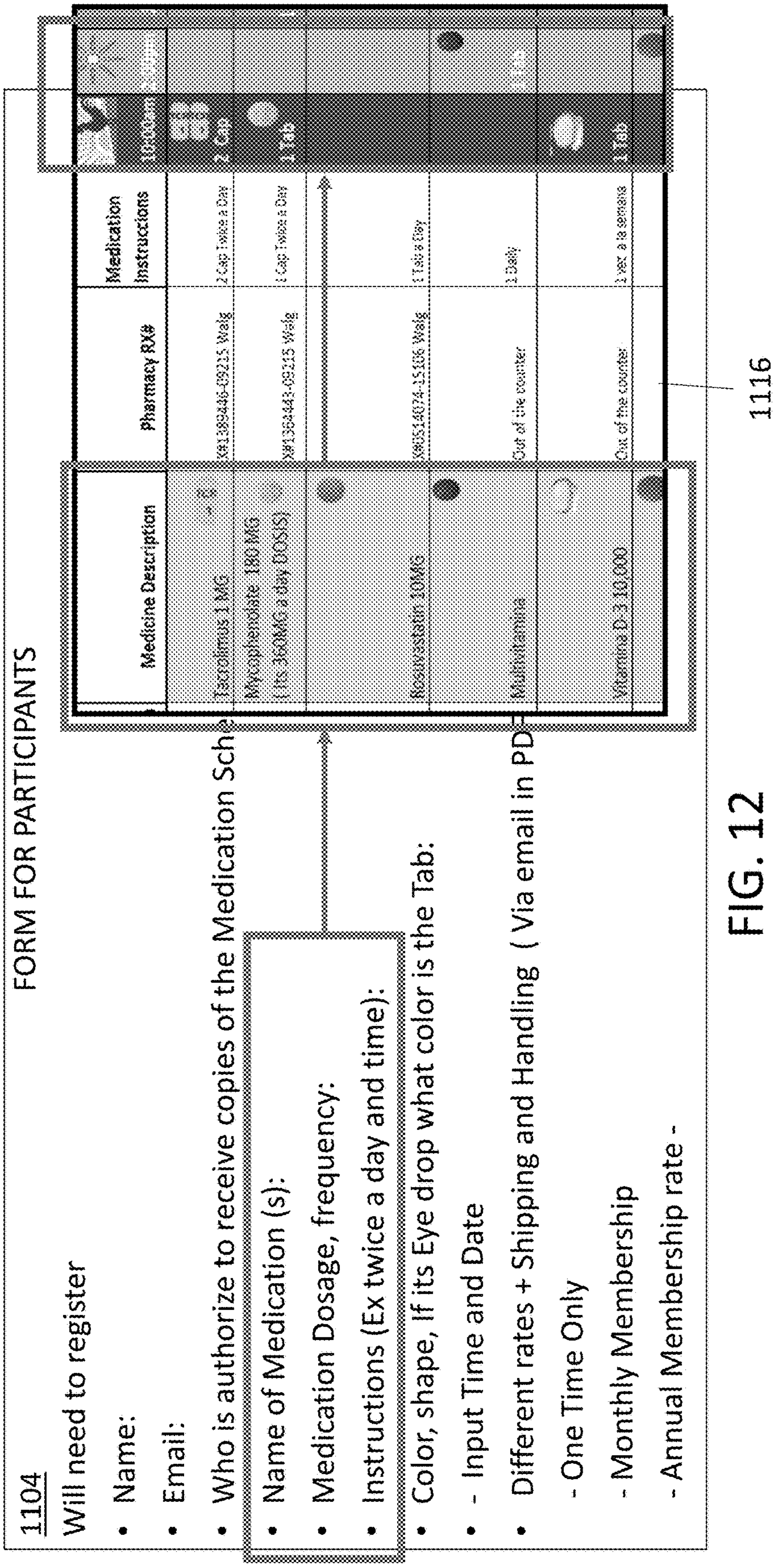
FIG. 12 is a portion of a user interface to input medication dosage information for the insert or one embodiment of the invention.
Figure 13:
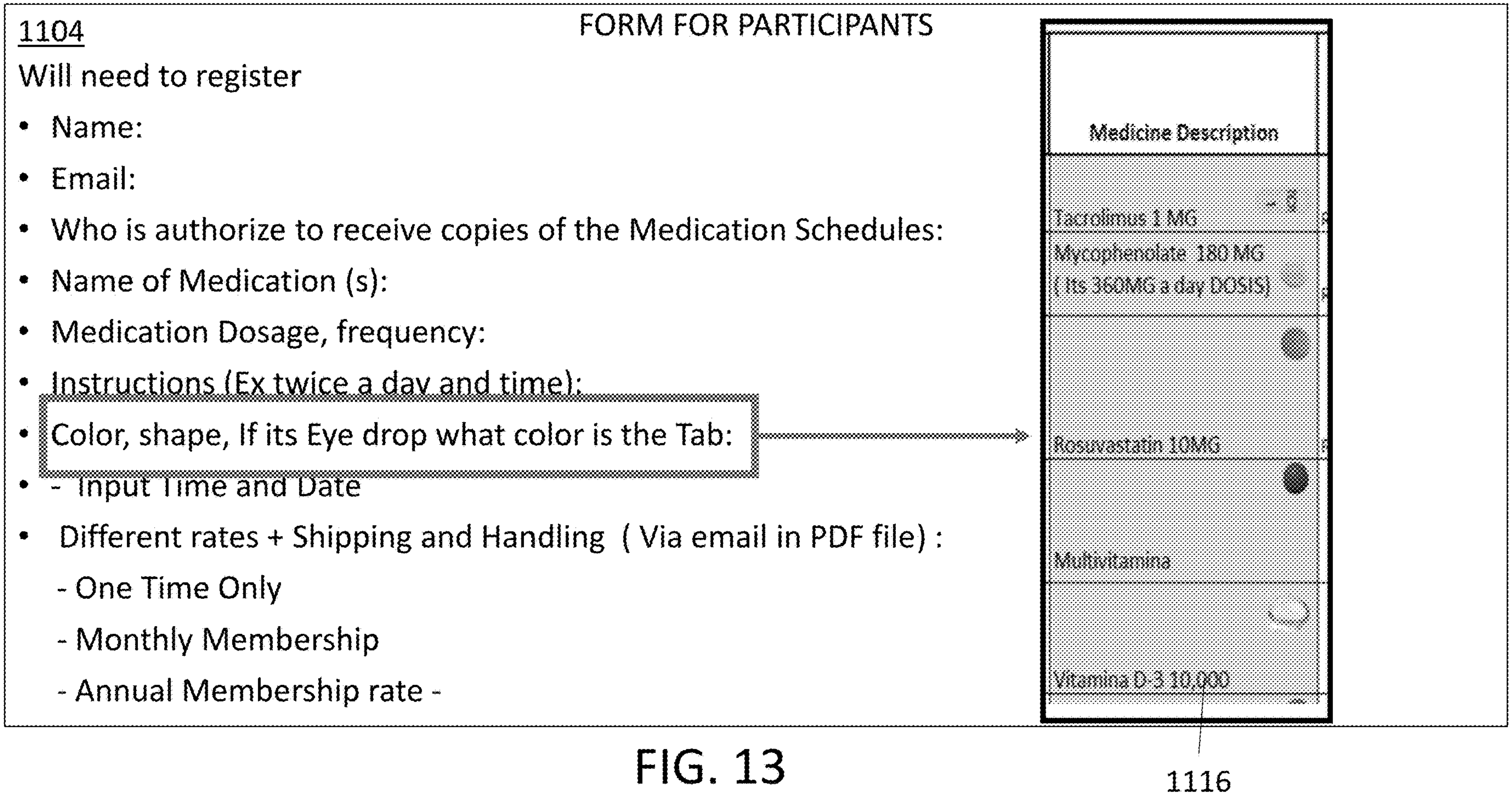
FIG. 13 is a portion of a user interface to input medication color for the insert of one embodiment of the invention.
Figure 14:
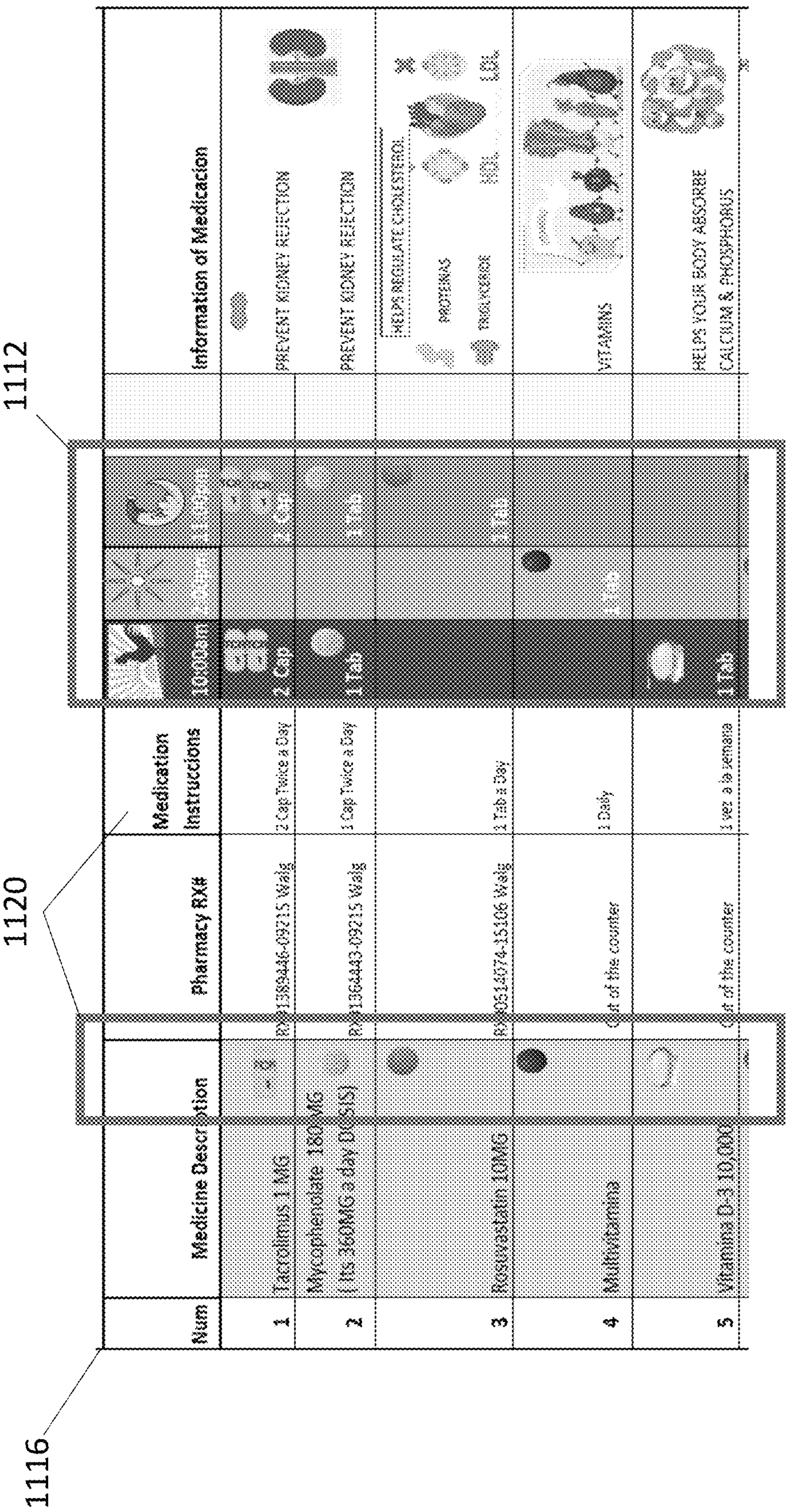
FIG. 14 is a portion of a user interface to input medication shape for the insert of one embodiment of the invention.

Referring now to FIGS. 11-13, a plurality of input screens of form 1104 in an embodiment of the system and method described herein. In one embodiment, a user inputs the information to populate the insert. Once the information is completed, an insert 1116 is generated. In one embodiment, one or more databases are created or queried to generate the insert 1116 output information corresponding to input information concerning the medications listed. In other embodiments, information to populate the inserts comes from patient databases operated by medical providers or pharmacies. It should be noted by one of skill in the art that the form 1104 shown in FIG. 11 is an example of the interface, screen, or information requested by an embodiment of the invention to produce the insert 1116 as described. The information could be filled out by hand or by typing in a premade insert template.

Referring to FIG. 12, a portion of the form 1104 shown in FIG. 11 is shown. Form 1104 may include one or more interfaces wherein the user, their relative, a representative, or a medical provider may input medication and dosage information. That information is then organized in the insert 1116 portion shown to the right. In various embodiments, the user, their relative, a representative, or a medical professional may input information regarding the shape and color of the medication, any indicating marks, colors, or shapes of bottles, of the like. That information is accumulated in the insert 1116 and represented as shown on the right hand side with the pictures of the medications. The insert 1116 of the invention provides a portable snapshot of the medical history of the user, which can be particularly useful in emergent condition where time is of the essence. A first responder responding to an emergency call, for example, would be equipped with information concerning patient history that otherwise would not be available in the first moments of a medical intervention. The insert 1116 may be generated in steps, portions, or simultaneously.

Figure 15:
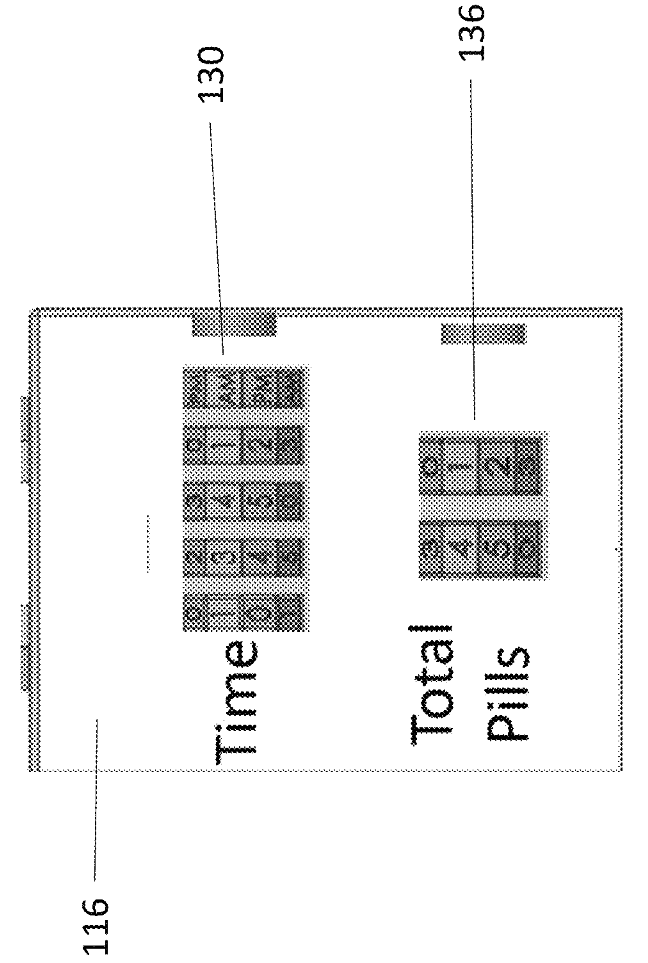
FIG. 15 is a planform of a time indicator compartment including a total pill indicator component.

FIG. 15 is a planform of a time indicator compartment 128 including a total pill indicator component 136. The time indicator compartment 128 may also include a similar mechanism for tracking the amount of pills taken from a certain, type, time of day, day of week, or other organizing principle related to the medication. For example the time indicator compartment 128 may be disposed to the left of a row of seven pill compartments 112 representing a week. The total pill indicator 136 may be utilized by the user to track the total amount of pills taken that week, the amount of pills taken on a day of that week, or the amount taken at a time of day of a day in the week.

FIG. 16 is a perspective view of a time indicator compartment 128 including a pill cutter disposed within. Time indicator compartment 128 may include a pill cutter 132 disposed on the underside of the lid 116 attached thereto and a complimentary component disposed on the floor of the time indicator compartment. A user may utilize the pill cutter to reduce the size of pills for ease of use and dosage control, according to embodiments. The user may lift the lid 116 of the time indicator compartment 128 by lifting it, using a button or release mechanism to flip it open, or another mechanism not here described. The user then may place the pill inside the pill cutter 132 and close the lid 116 to split the pill into one or more smaller portions. The pill cutter 132 may include internal organization to allow a user to see the portions of the pill they just cut or store a portion to take at a later time.

Figure 17:
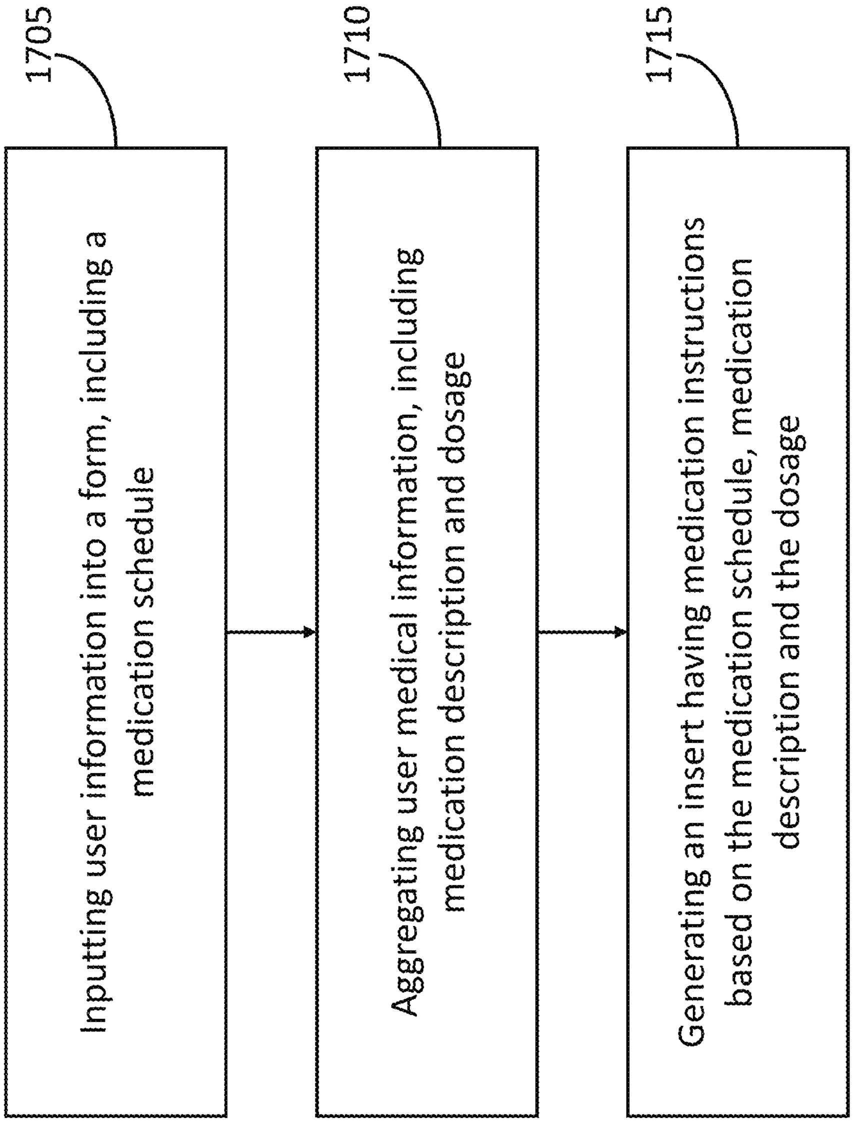
FIG. 17 is a flow diagram illustrating a method for medication compliance.

Referring now to FIG. 17, a method 1700 for medication compliance is illustrated in flow diagram form. The method 1700 includes, at step 1705, the user inputs the user information into a form. The form may be similar to or the same as form 1104. Form 1104 may be an electronic form, such as fillable fields on a user device, such as a smartphone or computing node. In various embodiments, form 1104 may be a physically written form, such as a piece of paper, typed into a fillable document like a PDF and printed, or a combination thereof. The user information 1108 may be any as described herein, for example the biographical information, medical history, medication type, dosage, shape, color, schedule 1112, or the like. The user's information 1108 may include personal information like a home address, a selected or proximate pharmacy, the user's insurance, the user's medical provider, the user's primary care physician or specialist, the user's family or emergency contact, and the like.

Still referring to FIG. 17, method 1700, at step 1710, includes aggregating user medical information. User medical information may be any medical information as described herein. User medical information may include medication description, such as a physical description, size description, color description, effect of the medication, or the like. User medical information may be a user medical history including vaccination history, injury history, current ailments or past conditions, diseases, or the like. In various embodiments, aggregating the user medical information may be performed by an automated system such as a software-hardware complex or the like. In various embodiments, the medical information may be aggregated by more than one computing node over the internet. In various embodiments, a plurality of databases may be queried by one or more computing nodes to retrieve said user medical information. In various embodiments, a medical provider or medical personnel may manually or semi-manually aggregate the user medical information. For example and without limitation, the medical personnel, such as a nurse, doctor or physician's assistant may retrieve the user medical information from one or more databases. In various embodiments, the user medical information may include a description of the medication that the user has been prescribed. In various embodiments, the user medical information may include a description of the dosage of said prescribed medications, such as a number of pills in pictorial form, a weight or number of pills in text form.

Aggregating the user medical information may include retrieving data from databases associated with medical providers, insurance companies, hospital systems, private or public databases, and the like. This may include organizing, relating, separating, or otherwise manipulating the user's data and associating said info with symbols, pictures, or other representations of the medical data in order to convey an easy-to-understand message to the user as shown in FIGS. 9 and 12-14. In various embodiments, one or more representations of medical data may be designed for the user who may be of an advanced age or unfamiliar with the medium with which the method is associated, like the user device, such as a user or smartphone.

Still referring to FIG. 17, method 1700, at step 1715, includes generating the insert 1116 that displays a user medical instructions, which may including the medication schedule 1112, user medical information, user biographical information or the like. This insert 1116 may be any of the inserts described herein, or a combination thereof. The insert 1116 may include medication pictures, names, instructions, times of day, days of week, and/or pictorial or symbolic representations of any of the data described herein. Insert 1116 may be transmitted to one or more user devices, such as a smartphone, smart TV, electronic device with access to a cellular or WiFi network, or the like. In various embodiments, the user device may be a cellphone having text message capabilities, electronic mail (e-mail) capabilities, or a screen configured to depict the insert graphically thereon. In various embodiments, the insert may be printed and presented to the user on paper, optionally stored in the drawer of the base tray 104. In various embodiments, the insert 1116 includes medical instructions configured for use with the system 100 as described herein. For example and without limitation, insert 1116 may include information related to the pill compartments in which specific medication is located, thereby directing the user to the correct medication, at the correct time of day, day of the week, and dosage information.

While the disclosed subject matter is described herein in terms of certain preferred embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A system for maintaining medication compliance, the device comprising:

a tray base, wherein the tray base comprises a plurality of recesses aligned in a plurality of rows and columns, each recess comprising a first anchor mechanism;

at least one pill compartment, each pill compartment having a second anchor mechanism disposed on a compartment bottom configured to couple to the first anchor mechanism, the pill compartment having a lid disposed on a top portion of the pill compartment;

a compartment coupling mechanism disposed on the pill compartment and configured to couple to a corresponding compartment coupling mechanism of an adjacent pill compartment;

at least one time indicator compartment, the time indicator compartment having a time set component configured to display a time of day disposed on a top portion each time indicator compartment, the time indicator compartment having a second anchor mechanism disposed on a bottom portion of the time indicator compartment and the pill compartment coupling mechanism disposed on a wall of the time indicator compartment.

2. The system of claim 1, wherein the tray base comprises a plurality of recesses, the recesses formed in 4 rows and 8 columns.

3. The system of claim 1, wherein a subset of the recesses are configured to receive the time indicator compartment wherein each row has one time indicator compartment.

4. The system of claim 3, wherein the lid is rotatably coupled to the back wall and releaseably coupled to the front wall.

5. The system of claim 1, further comprising a tray drawer slidably disposed within a hollow portion of the tray base.

6. The system of claim 5, wherein at least one of the plurality of time indicator compartments can be coupled to at least one pill compartment.

7. The system of claim 1, wherein each pill compartment has a front wall and a back wall disposed opposite and opposing, connected therebetween by two sidewalls coupled at each end and disposed opposite and opposing from each other and a compartment floor disposed thereunder perpendicular to and terminating at each of the walls.

8. The system of claim 1, wherein the pill compartment has a lid release disposed on the front wall configured to hold the lid closed until released.

9. The system of claim 1, wherein each time indicator compartment comprises a pill cutter disposed within it, wherein the top portion is rotatably attached to the back wall and releaseably attached to the front wall.

10. The system of claim 1, wherein each time indicator compartment comprises a pill counter component configured to be mechanically rotated to display numbers corresponding to taken medication.

11. The system of claim 1, wherein a first pill compartment having a first compartment coupling mechanism is configured to couple to a second adjacent pill compartment via a second compartment coupling mechanism.

* * * * *